(12) United States Patent
Slepian et al.

(10) Patent No.: US 6,491,672 B2
(45) Date of Patent: Dec. 10, 2002

(54) TRANSURETHRAL VOLUME REDUCTION OF THE PROSTATE (TUVOR)

(75) Inventors: Marvin J. Slepian, Tucson, AZ (US); Daniel Yachia, Herzlia-on-Sea (IL); Syed Hossainy, Fremont, CA (US); Baruch Levy, Ramat-Gan (IL); Zeev Sohn, Ginot Shomron (IL)

(73) Assignee: Harmonia Medical Technologies, Inc., Rosh Ha'Ayin (IL)

( * ) Notice: Subject to any disclaimer, the term of this patent is extended or adjusted under 35 U.S.C. 154(b) by 99 days.

(21) Appl. No.: 09/778,651

(22) Filed: Feb. 7, 2001

(65) Prior Publication Data

US 2001/0047147 A1 Nov. 29, 2001

Related U.S. Application Data

(60) Provisional application No. 60/181,646, filed on Feb. 10, 2000.

(51) Int. Cl.[7] ................................................ A61M 25/00
(52) U.S. Cl. .................... 604/267; 606/171; 606/180
(58) Field of Search ............................... 604/266, 267; 606/170, 171, 180

(56) References Cited

U.S. PATENT DOCUMENTS

| | | |
|---|---|---|
| 2,675,619 A | 4/1954 | Cone |
| 2,677,700 A | 5/1954 | Jackson et al. |
| 2,979,578 A | 4/1961 | Curtis |
| 3,306,118 A | 2/1967 | Cartier |
| 3,535,307 A | 10/1970 | Moss et al. |
| 3,829,506 A | 8/1974 | Schmolka et al. |
| 4,228,802 A * | 10/1980 | Trott ........................... 604/267 |
| 4,517,686 A | 5/1985 | Ruoslahti et al. |
| 4,578,079 A | 3/1986 | Ruoslahti et al. |
| 4,589,881 A | 5/1986 | Pierschbacher et al. |
| 4,938,763 A | 7/1990 | Dunn et al. |
| 5,041,380 A | 8/1991 | Ruoslahti et al. |
| 5,149,780 A | 9/1992 | Plow et al. |
| 5,169,930 A | 12/1992 | Ruoslahti et al. |
| 5,762,626 A | 6/1998 | Lundquist et al. |
| 5,792,157 A * | 8/1998 | Mische et al. .............. 606/170 |
| 5,794,626 A | 8/1998 | Kieturakis |
| 5,807,309 A | 9/1998 | Lundquist et al. |
| 6,206,900 B1 * | 5/2001 | Tabatabaei et al. ......... 606/180 |

FOREIGN PATENT DOCUMENTS

| | | |
|---|---|---|
| DE | 197 06 751 A | 10/1997 |
| DE | 197 03 208 A | 8/1998 |
| EP | 0 893 101 A | 1/1999 |

OTHER PUBLICATIONS

Aumailley, et al., "Arg–Gly–Asp constrained within cyclic pentapeptides. Strong and selective inhibitors of cell adhesion to vitronectin and laminin fragment P1," *FEBS* 291(1):50–54 (1991).

Beck, et al., "Structure and function of laminin: anatomy of a multidomain glycoprotein," *FASEB J.* 4:148–160 (1990).

(List continued on next page.)

*Primary Examiner*—Philippe Derakshani
(74) *Attorney, Agent, or Firm*—Holland & Knight LLP

(57) ABSTRACT

A process has been developed to reduce or relieve prostatic obstruction. The steps involved in the TUVOR Process include: 1. Transurethral Incision; 2. De-bulking and Intra-Prostatic Volume Reduction; 3. Intra-prostatic void exclusion and space filling with adhesive and/or therapeutic polymeric materials, alone or in combination with bioactive agents and/or mechanical means for closure; 4. Endourethral compression and prostatic mass remolding; 5. Endourethral Polymer Liner Layer. This liner formed from structurally supportive, yet eventually biodegradable, polymers further bolsters and supports the urethra and peri-urethral tissue during healing, eliminating the need for post-procedure catheter drainage. This step may be optional in specific clinical circumstances. The process is designed to allow outpatient treatment under local anesthesia for BPH.

41 Claims, 5 Drawing Sheets

OTHER PUBLICATIONS

Graf, et al., "A pentapeptide from the laminin B1 chain mediates cell adhesion and binds the 67,000 laminin receptor," *Biochem* 26:6896–6900 (1987).

Graf, et al., "Identification of an amino acid sequence in laminin mediating cell attachment, chemotaxis, and receptor binding," *Cell* 48:989–996 (1987).

Grant, et al., "Two different laminin domains mediate the differentiation of human endothelial cells into capillary–like structures in vitro," *Cell* 58:933–943 (1989).

Gurrath, et al., "Conformation/activity studies of rationally designed potent anti–adhesive RGD peptides," *Eur. J. Biochem.* 210:911–921 (1992).

Iwamoto, et al., "YIGSR, a synthetic laminin pentapeptide, inhibits experimental metastasis formation," *Science* 238:1132–1134 (1987).

Kleinman, et al., "Basement membrane complexes with biological acitvity," *Biochem.* 25:312–318 (1986).

Kleinman, et al., "Biological activities of laminin," *J. Cell Biochem.* 27:317–325 (1985).

Mohri, et al., "Novel effect of cyclicization of the Arg–Gly–Asp–containing peptide on vitronectin binding to platelets," *Amer. J. Hem.* 37:14–19 (1991).

Pierschbacher & Ruoslahti, "Influence of stereochemistry of the sequence Arg–Gly–Asp–Xaa on binding specificity in cell adhesion," *J. Biol. Chem.* 262(36):17294–17298 (1987).

Sakamoto, et al., Inhibition of angiogenesis and tumor growth by a synthetic laminin peptide, CDPGYIGSR–NH2, *Cancer Res.* 51:903–906 (1991).

Scarborough, et al., "Design of potent and specific integrin antagonists. Peptide antagonists with high specificity for glycoprotein IIb–IIIa," *J. Biol. Chem.* 68(2):1066–1073 (1993).

Tay, et al., "Activity toward thrombin–antithrombin of heparin immobilized on two hydrogels," *Biomaterials* 10:11–15 (1989).

* cited by examiner

TRANSURETHRAL VOLUME REDUCTION OF THE PROSTATE (TUVOR)

This application claims priority to U.S. Ser. No. 60/181,646 filed Feb. 10, 2000.

BACKGROUND OF THE INVENTION

This invention relates to apparatus and a method for the removal and treatment of prostate tissue to treat conditions associated with diseases or disorders resulting in obstruction of the uro-genital systems.

As men age, their prostate glands typically enlarge due to growth of intraprostatic paraurethral glands tissue (prostate adenoma) obstructing the flow of urine through the urethra. This condition is known as benign prostatic hypertrophy ("BPH"), and results in a partial or total inability to urinate. The incidence of symptomatic BPH for men in their fifties is approximately 50%, rising to 90% by age 85. About 25% of men in the United States will be treated for BPH by age 80.

Traditional surgical therapy for BPH has involved open enucleation or transurethral resection of the prostate. Surgical treatment of BPH is generally reserved for patients with severe symptoms or for those who have developed urinary retention, renal damage caused by BPH, or those with significant potential complications if treatment were withheld. These painful procedures usually result in long-term recovery although the patient may be subjected to traumatic side-effects.

The most common surgical procedure, Transurethral Resection of the Prostate ("TURP"), involves the removal of the prostate's innermost core in order to enlarge the caliber of the prostatic urethra. The average TURP procedure costs approximately $12,000 and requires a hospital stay of approximately 3 to 4 days. During this period the patient is burdened with a Foley drainage catheter and bag. TURP side-effects include impotence (up to 30%), retrograde ejaculation, and short-term or permanent incontinence.

Suprapubic or Retropubic (Open) Prostatectomy (SPP/RPP) involves surgical removal of the enlarged prostate via an incision in the lower abdomen, usually requiring a 5 to 7 day hospital stay. Patients are allowed to return to work 2 to 3 weeks after the surgery. Open prostatectomy may result in impotence (up to 30% of cases), retrograde ejaculation and incontinence.

Transurethral Incision of the Prostate (TUIP) is an endoscopic surgical procedure in which one to three cuts is made in the prostate to relax the constriction on the prostatic urethra. TUIP is limited to prostates below 30 grams in size and requires 2 days of hospitalization. TUIP patients may experience short-term incontinence, and on rare occasions, retrograde ejaculation.

Transurethral Vaporization of the Prostate (TUVP) is a procedure for ablating the prostatic tissues by vaporization using an electrosurgical roller. The cost and the hospital stay for this procedure is similar to that of the TURP. Although TUVP causes less bleeding than TURP, the impotence rates are not dissimilar.

In balloon dilatation, a catheter with a high-pressure balloon at the end is inserted through the urethra and into the prostatic urethra. The balloon is then inflated to stretch and tear the prostatic urethra and to enlarge its caliber. Clinical studies have demonstrated a high rate of obstructive recurrence. This therapy has largely been abandoned.

Laser assisted Prostatectomy includes two similar procedures, Visual Laser Ablation of the Prostate (V-LAP) and Contact Laser Ablation of the Prostate (C-LAP). Typically, the procedure is performed in the hospital under either general or spinal anesthesia, and at least an overnight hospital stay is required. In V-LAP, the burnt prostatic tissue then necroses, or dies, and over four to twelve weeks is sloughed off during urination. In C-LAP, the prostatic and urethral tissue is burned on contact and vaporized. The major drawbacks to these procedures include their high cost equipment and high re-treatment rates.

TransUrethral Microwave Therapy (TUMT) is based on a catheter inserted into the urethra, on which a microwave antenna is situated at the level of the prostate. The urethra can be spared by cooling, but will otherwise be destroyed. Scarring of the prostatic tissue enlarges the urethral lumen. The drawback of this treatment is long catherization time (1–6 weeks) and high-re-treatment rates.

TransUrethral Needle Ablation (TUNA) is performed by transurethrally inserting two radio-frequency antennas into the prostatic tissue for heat damage creation. The drawbacks involved are a long catheterization period (up to 6 weeks) and very high re-treatment rates. Interstitial Laser Coagulation (ILC) is very similar to TUNA but the heat source is a laser.

High Intensity Focused Ultrasound (HIFU) brings a beam of ultrasound into a tight focus at a selected depth within the prostate, generating temperatures of 80–100° C. and causing coagulation necrosis. The energy is delivered transrectally, and a catheter is inserted into the urethra for enhancing the treatment. The drawbacks of this treatment is the major cost of the equipment and long catheterization periods.

Water Induced Thermotherapy (WIT) is similar to non-urethra sparing microwave treatments. The heat damage is created by heating a balloon at the prostatic urethra and by heating the prostatic tissue. It has the same drawbacks as microwave treatments.

Holmium Laser Prostatectomy is comparable to open prostatectomy. During this treatment, as in open surgery, the entire hypertrophied gland is enucleated (but endoscopically) and dropped into the bladder. This gland should be morselated for removal. The drawbacks of this treatment are the cost of the equipment and the long learning curve.

In addition to the above, a few general limitations emerge regarding alternative therapies. By targeting tissue killing to regions surrounding the urethra, some relief of compressive urethral obstruction is achieved. However, with the exception of Holmium Laser Prostatectomy, none of these procedures directly removes material. All of these techniques rely on the body's response to injury and inflammation (the reticuloendothelial system (RES)) to slowly remove necrotic cells and "clean-up" the area. As such, all of these techniques take several months to ultimately lead to a maximal effect, which is also limited. In many of these techniques no actual net tissue removal or reduction occurs. Rather, the injury may lead to localized scarring and fibrosis which may ultimately lead to obstruction recurrence. The response to injury is individually variable and lesser degrees of relief are often achieved. Patients who are treated by thermotherapy typically recover quickly, but need to be catheterized for at least one week post-treatment to maintain urine flow. Even after catheter removal, irritating urinary symptoms frequently persist during the period of tissue sloughing and healing.

Drug therapy is sometimes an option. Some drugs are designed to shrink the prostate by inhibiting or slowing the growth of prostate cells. Other drugs are designed to relax the muscular tissue in the prostate capsule and bladder neck to relieve urethral obstruction. Current drug therapy (including Finasteride Therapy, Alpha Blocker Therapy and Phytotherapy) generally requires daily administration for the duration of the patient's life, and are known to cause dizziness and fainting, decreases in blood-pressure, impotence, retrograde ejaculation or a reduction in the volume of ejaculated sperm. Furthermore, the effectiveness of these drug therapies in long-term treatment of BPH has not been proven scientifically.

To date, the most effective surgical intervention for BPH, is TURP. This procedure is invasive, requiring regional or general anesthesia, several days of hospitalization and post-treatment placement of a drainage catheter. TURP frequently presents a high operative cost and risk for many patients. The potential disadvantages and limitations of TURP include bleeding, urinary tract infections, urethral irritation, discomfort, occasional urinary incontinence, sexual dysfunction. Despite these limitations, TURP is currently the gold standard of therapy for BPH.

It is therefore an object of the present invention to provide apparatus and materials for treatment of BPH.

It is a further object of the present invention to provide polymeric materials, drugs and biologically active compositions which can be delivered or released within or adjacent to prostatic or urethral tissue to aid in healing. It is another object of the present invention to provide an effective, low cost outpatient BPH treatment with enhanced efficacy, reduced length of hospital stay, reduced patient discomfort, and lower recurrence rate.

SUMMARY OF THE INVENTION

Trans Urethral Volume Reduction of the prostate (TUVOR) has been designed with distinct tissue and function sparing objectives that are unavailable in any current therapy. This process allows for significant volume reduction of the prostate as an out-patient therapy, not requiring several days in the hospital with a catheter. There are several key concepts that enable minimal trauma, outpatient therapy for even severely enlarged prostates.

The first concept upon which TUVOR is based is acute tissue removal with reduced tissue trauma. The approach is to achieve clean surgical excision of BPH tissue (adenoma) with reduced urethral and sphincteric injury. This tissue sparing translates into reduced post-procedure obstruction and more rapid healing. The bladder neck is also preserved in this procedure, thereby minimizing the potential for incontinence and retrograde ejaculation; side effects associated with existing solutions. Using the TUVOR method, BPH tissue is removed by piercing the urethra with a mechanical debulking device. This device is then used to excise, morsellate and liquefy the prostate adenoma. Irrigating fluid flow into and out of the void created in the adenoma can be used to remove tissue.

Unnecessary trauma, injury and side effects such as impotence are avoided by avoiding exposing surrounding normal tissue structures to unnecessary heat, acoustic shock wave or other energy (as occurs with laser, radio frequency, or ultrasound methods). Furthermore, this mechanical removal of bulk does not rely on the body's innate ability to remove and remodel diseased or necrotic tissue (i.e., RES, the reticuloendothelial system ) to achieve volume reduction. RES clean up does not lead to actual bulk tissue removal or significant prostate volume reduction, but rather to localized scarring. Another feature of the TUVOR process is the use of biocompatible biodegradable polymers as an adhesive that are inserted into the void created in the adenoma. A balloon inflated in the urethra can be used to compress this void while the polymers bond the surfaces. Alternatively or in addition, the surfaces may be secured using more conventional means such as staples or sutures. The balloon expansion also serves several additional purposes. It helps expel any remaining morsellated tissue from the void. It can help stop any residual bleeding in the void. The balloon also enlarges and reshapes the intra-urethral space, thereby eliminating any obstruction. The bonding polymers may be selected to have additional properties such as the ability to facilitate healing, minimize inflammation, decrease fibrotic response, inhibit adenoma regrowth or other therapeutic benefits.

An important feature of the TUVOR process is the ability to combine a transurethral incision with the intra-prostatic bulk removal. This incision relieves some of the pressure on the adenoma. Combined with bulk removal, the intra-urethral volume can subsequently be maximized.

Outpatient performance of TUVOR without catheterization is made possible by the application of a biodegradable polymer in situ casting to the prostatic urethra. This liner further supports and protects the urethra and peri-urethral tissue during healing. This polymer may also be designed to incorporate additional drug or gene therapies.

Outpatient performance of TUVOR is farther enabled by designing the TUVOR device to be of small circumference to perform the procedure under local anesthesia. The TUVOR device can incorporate the ability to administer local anesthesia or the local anesthesia can be administered prior to use of the device.

The steps involved in the TUVOR Process are summarized as follows:

1. Local anesthesia. A tubular sheath with endoscopic vision capabilities is guided to the prostatic urethra and local anesthesia is injected as needed.
2. Transurethral Incision. One or more longitudinal transurethral incisions are made to enter the main body of the prostate, leaving the urethra largely intact. Incisions are continued down to the capsule of the adenoma for immediate relief of the obstruction.
3. De-bulking and Intra-Prostatic Volume Reduction. Volume reduction is achieved via rapid controlled mechanical tissue excision, morsellation and liquefaction of the obstructive adenoma within the middle and lateral aspects of the prostate, leaving the tissue and much of the vascularity of the urethra and peri-urethral region (normal tissue) intact. This mid and lateral debulking preserves the urethra, further reducing the propensity for post-procedure outflow obstruction, pain and further speeds healing.
4. Intra-prostatic void exclusion and space filling with adhesive and/or therapeutic polymers. Voids created as a result of intra-gland "shelling out" are filled with adhesive polymers that facilitate intraprostatic void cavity wall bonding and healing. Polymers are specifically selected to minimize inflammation, secondary bleeding and late fibrotic scarring.
5. Endourethral compression and prostatic mass reshaping. The prostatic urethra is further remolded and re-shaped via endourethral balloon inflation, compacting the residual prostatic "shell" of tissue and further facilitating bonding and adhesion of intra-gland residual surfaces. The net result is a smaller prostate volume with a larger endourethral lumen and cross-sectional area facilitating urine flow and preserving the urethral lining.
6. Endourethral Polymer Liner Layer. As a final step, a biodegradable polymer liner layer can be applied to the prostatic urethra by in situ casting. This liner is formed from structurally supportive, yet eventually biodegradable polymers. This liner further bolsters and supports the urethra and peri-urethral tissue during healing, eliminating the need for post-procedure catheter drainage. This step may be optional in specific clinical circumstances. It may also be replaced by use of commonly used urethral stents or catheters in specific circumstances.

Depending on the type and severity of the BPH, the steps in the above process may be ordered differently and even selectively performed. This process provides a more biocompatible, less traumatic means of reducing BPH obstruction that is more sparing of normal urethral tissue and physiologic function. Further, TUVOR provides a simple, and effective outpatient procedure for the long-term treatment of BPH.

BRIEF DESCRIPTION OF THE DRAWINGS

FIG. 1A, normal prostatic gland in cross-section. FIG. 1B, prostate with BPH in cross-section. FIG. 1C shows transurethral incisions made through the urethra into the gland parenchyma, through which tissue removal means are inserted to create tissue voids within the prostate. FIG. 1D shows the tissue voids filled with bioadhesive polymer. FIG. 1E shows compaction of the voids via placement of an expansion means in the urethra, such as a balloon. FIG. 1F shows the endourethral surface of the shelled out compacted prostate supported via placement in situ of a biodegradable endourethral liner.

FIG. 7A, localized sutures via endoluminal means; FIG. 7B, multiple sutures or weave; FIG. 7C, local staples or signlet closure means; FIG. 7D, linear tack-like closure means; FIG. 7E, closure means with central bolster element; FIG. 7F, button or snap closure system; and FIG. 7G, male-femal closure means.

DETAILED DESCRIPTION OF THE INVENTION

Figure 1A:
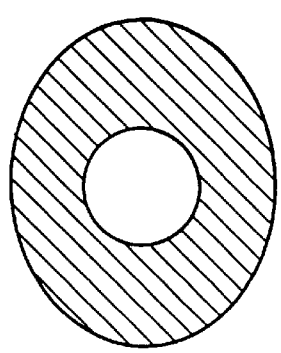
FIG. 1A–1F are schematics showing the TUVOR process.
Figure 1B:
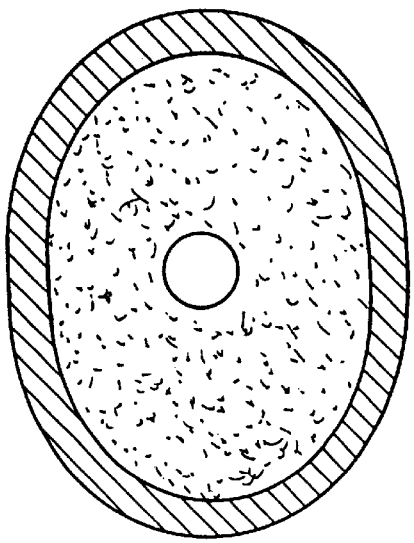

FIGS. 1A and 1B are cross-sectional schematics of a normal (FIG. 1A) and enlarged (FIG. 1B) prostate with the urethra shown in the center, significantly decreased in diameter as a result of the enlargement of the prostate in FIG. 1B. The TUVOR method entails several different steps that can be performed all together or in part to decrease the prostate size and alleviate urethral obstruction. A summary of the steps involved in the TUVOR Process is provided in outline form below:

1. Local Anesthesia.

A tubular sheath with endoscopic vision capabilities is guided to the prostatic urethra and local anesthesia is injected as needed.

2. Transurethral Incision.

Figure 1C:
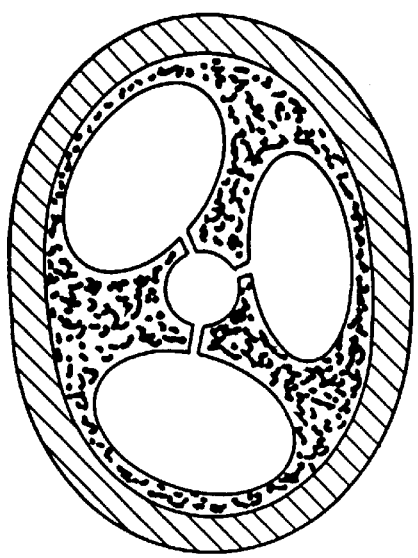

One or more transurethral incisions are made to enter the main body of the prostate, leaving the urethra largely intact, as shown in FIG. 1C. Incisions are continued down to approach the capsule of the adenoma for immediate relief of the obstruction.

3. De-bulking and Intra-Prostatic Volume Reduction.

Volume reduction is achieved via rapid controlled mechanical tissue excision, morsellation and liquefaction of the obstructive adenoma within the middle and lateral aspects of the prostate, leaving the tissue and much of the vascularity of the urethra and peri-urethral region (normal tissue) intact. This mid and lateral debulking preserves the urethra, further reducing the propensity for post-procedure outflow obstruction and pain and further speeds healing, as also depicted in cross-section in FIG. 1C.

4. Intra-prostatic Void Exclusion and Space Filling with Adhesive and/or Therapeutic Polymers.

Figure 1D:
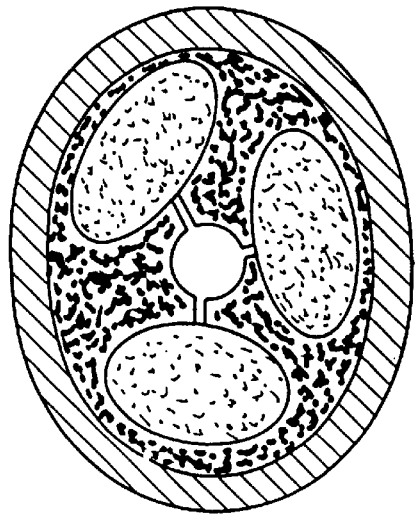

Voids created as a result of intra-gland "shelling out" are filled with adhesive polymers that facilitate intraprostatic void cavity wall bonding and healing, as depicted in FIG. 1D. Polymers are specifically selected to minimize inflammation, secondary bleeding and late fibrotic scarring.

5. Endourethral Compression and Prostatic Mass Re-shaping.

Figure 1E:
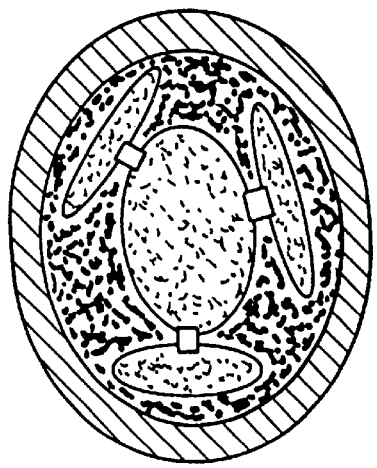

The prostatic urethra is further remolded and re-shaped via endourethral balloon inflation, compacting the residual prostatic "shell" of tissue and further facilitating bonding and adhesion of intra-gland residual surfaces, as shown in FIG. 1E. The net result is a smaller prostate volume with a larger endourethral lumen and cross-sectional area facilitating urine flow and preserving the urethral lining, as shown in FIG. 1F.

6. Endourethral Polymer Liner Layer.

Figure 1F:
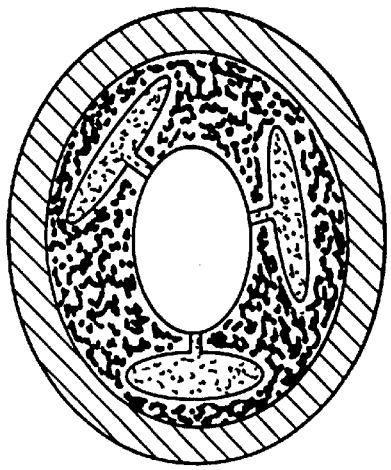

As a final step, a biodegradable polymer liner layer is applied to the prostatic urethra by in situ casting, as also shown in FIG. 1F (dark inner lining of urethra). This liner, formed from structurally supportive, yet eventually biodegradable polymers, further bolsters and supports the urethra and periurethral tissue during healing, eliminating the need for post-procedure catheter drainage. This step may be optional in specific clinical circumstances. It may also be replaced by use of commonly used urethral stents or catheters in specific circumstances.

A. Devices

Figure 2:
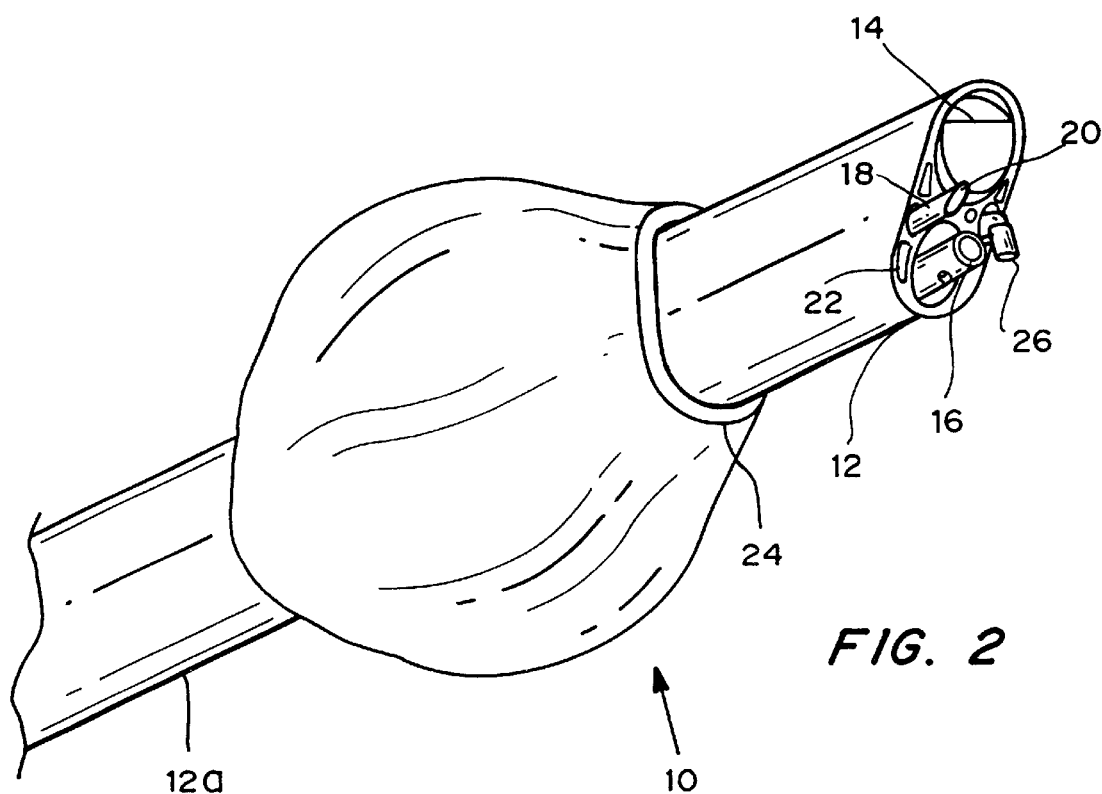
FIG. 2 is an isometric view of the TUVOR Device.

In one embodiment of the TUVOR device 10 shown in FIG. 2, all the tools necessary for performing this procedure are included within a single tubular sheath 12 that is inserted in the urethra. The sheath 12 allows access to the prostatic urethra. Ideally, for outpatient treatment where local anesthesia is used, the optimal sheath 12 should not exceed 19 French. However, larger diameter sheaths 12 can be used. As shown in FIG. 2, sheath 12 surrounds all the components. The sheath 12 may be formed of either a rigid or semi-rigid metal or plastic material. Contained within the sheath 12 is an optical component 14 that allows the user to view the procedure. Cutter 16 may be capable of extending longitudinally beyond the distal end of the sheath 12 and to enter through the urethral wall into the prostate. Cutter 16 may contain features that allow its diameter to expand after entering the prostate thereby allowing faster excision. Alternatively the cutter may contain means for scooping out, drilling out, suctioning out, debulking, burning, chemically or otherwise creating spaces, holes or voids in the prostatic tissue. Cutter 16 may also contain lumens and other components that aid in the removal of excised tissue. Tube 18 is also capable of extending longitudinally from the distal end of the sheath 12. This tube 18 has a lumen 20 through which anesthesia, polymer adhesive, polymer liner or any other drug can be administered. Additionally, this lumen 20 may be used to remove tissue from the excised area of the prostatic adenoma. The sheath 12 may have additional lumens 22 that can be used for transporting fluid in either direction. Balloon 24 surrounds the sheath 12. A lumen (not shown) provides a path from the sheath's proximal end 12a to the balloon 24 and is used to inflate this balloon 24. Balloon 24 expands within the urethra to expand the intraurethral volume while collapsing any voids that were excised in the prostatic adenoma. A cold-knife or radio-frequency cutter 26 can also extend longitudinally from the sheath in order to perform the transurethral incision.

Figure 3:
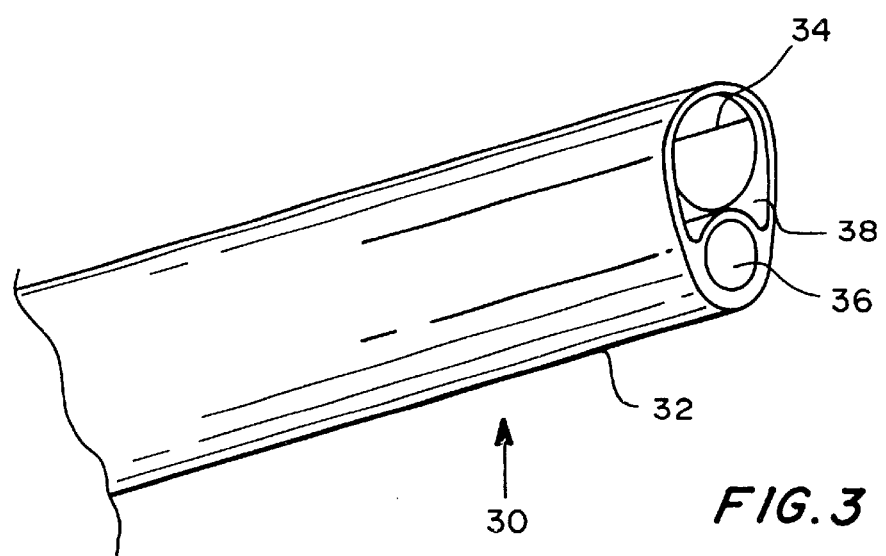
FIG. 3 is an isometric view of another TUVOR device.

In another embodiment of this device 30 shown in FIG. 3, the various components of the device are provided separately and inserted sequentially as needed. This allows for a smaller sheath size to be used. The sheath 32 holds the optical element 34. A large lumen 36 can be used to insert various devices such as an injection needle, a balloon catheter, a cutter for removing intraprostatic material or a radio-frequency cutter or coagulator. Additional lumens 38 are used for fluid transference.

The TUVOR process achieves significant bulk tissue removal from the gland mass with minimal urethral trauma. This is achieved by entering the adenoma through the urethra with a cutting device. Volume of the prostate is reduced via tissue excision, morsellation and liquefaction of the prostate adenoma. Tissue is removed specifically from the obstructing portions of the prostate, thereby preserving the periurethral tissue, much of the urethral vascularity and bulk of the urethra itself.

Figure 4A:
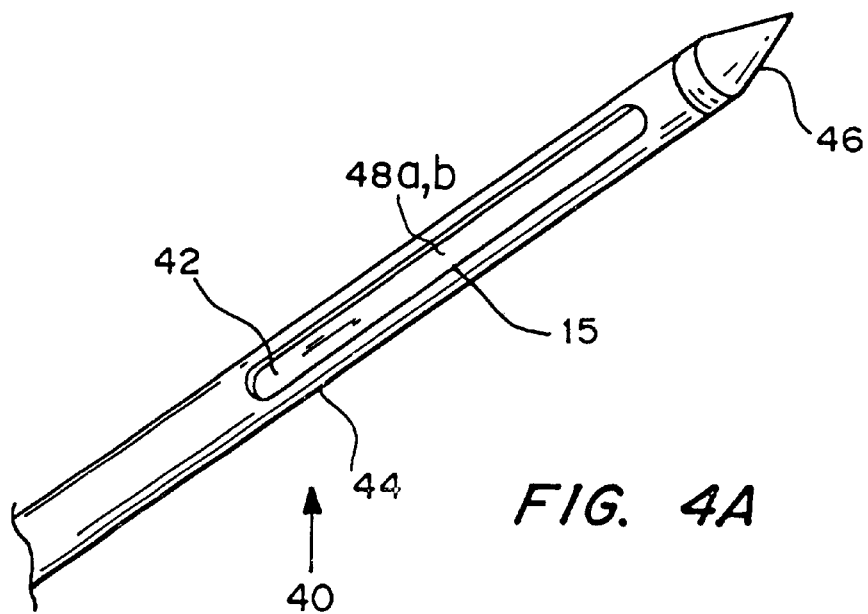
FIGS. 4A and 4B are isometric views of one embodiment of a TUVOR cutter, showing the cutting portion contained within the shaft (FIG. 4A) and expanded into cutting position (FIG. 4B).
Figure 4B:
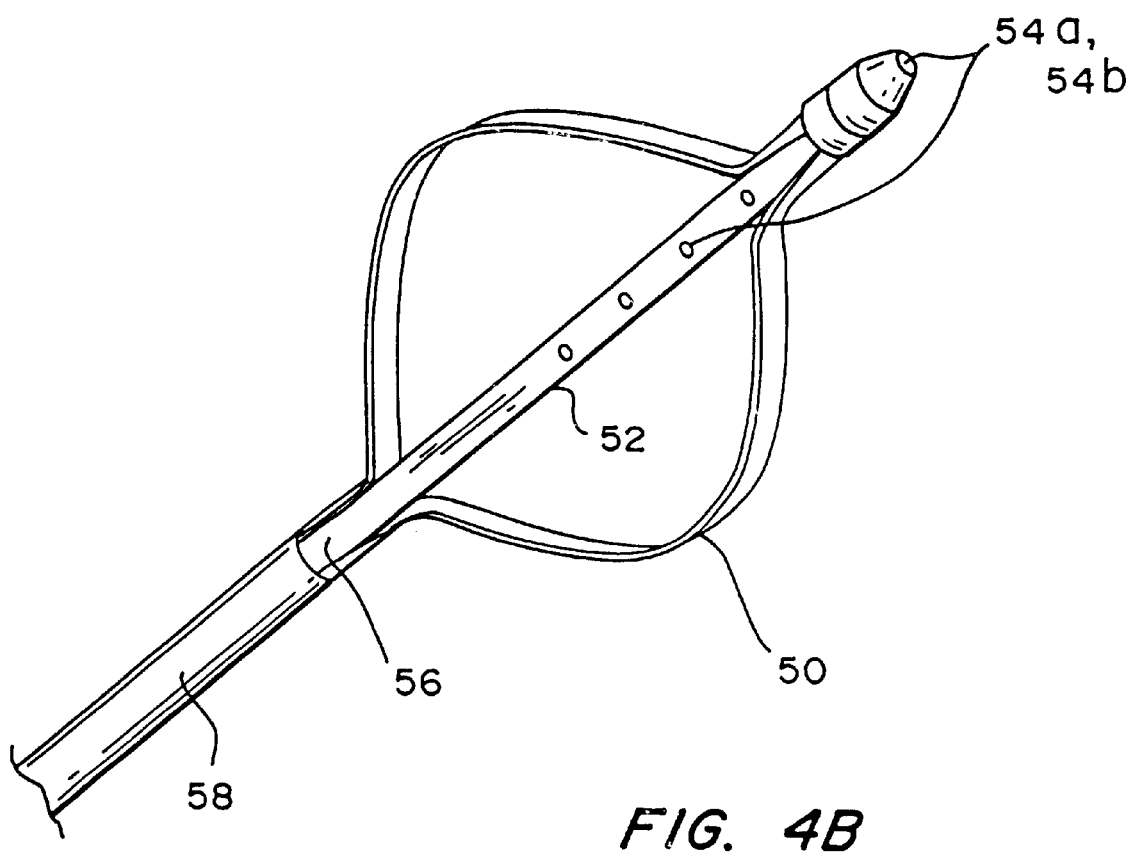

A preferred embodiment for a cutter 40 to create a void in the gland mass is shown in FIGS. 4A and 4B. In FIG. 4A the cutter 40 is shown in its nominal shape when it has a reduced diameter designed to pass through the urethra with minimal damage. The cutter 40 consists of an inner shaft 42 that passes through outer tube 44 and is joined with the tube 44 at the distal tip 46. There are at least two longitudinal slits 48a,b cut in the tube 44 near the distal end 46. Longitudinal translation of the shaft 42 relative to the tube 44 causes the tube 44 to bow out in the region nears the slits 48a,b as shown in FIG. 4B. The cutter 40 can be deformed to this enlarged diameter during the cutting process. By rotating the expanded cutter 50 shown in FIG. 4B at high angular speed it is possible to excise, morsellate and liquefy the gland mass at a very high rate. As shown in FIG. 4B, the shaft 52 of the cutter 50 has a lumen running longitudinally through its length. At the distal end of the cutter 50 there can be one or more holes 54a,b. Fluid can be transferred in either direction through the lumen in order to facilitate the cutting process or to help remove material from the body. Fluid can also flow through the space 56 between the cutter 50 and the tube 58. An auger may be added to the rotating shaft in order to facilitate fluid flow.

In yet another embodiment, the rotating cutter may have a different cutting mechanism. Wires restricted within a tube may be moved longitudinally so that they extend radially through hole or slits in the tube. These wires, when rotated at high speed can cut, morsellate and liquefy the gland mass. The amount of radial extension for the wires may be controlled so that the void shape is optimized. The cutting action can be facilitated by the injection of water in the cutting plane while a rotating auger is evacuating the fragments of the minced tissue.

Figure 5:
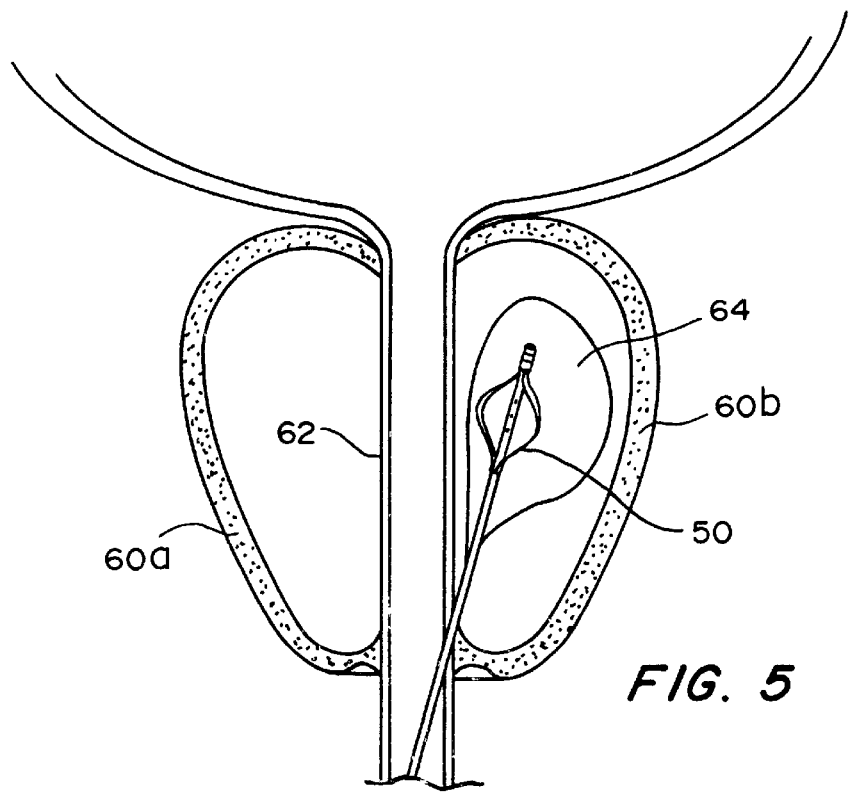
FIG. 5 is a schematic view of a void being carved in prostatic tissue using the TUVOR cutter of FIG. 5.

FIG. 5 shows a schematic of two lateral lobes 60a,b of an enlarged prostate 60 and the urethra 62. The cutter 50 has cut a void 64 in the adenoma. Generated tissue voids within the body of the prostate can subsequently be filled with biocompatible biodegradable polymers to act as intra-void tissue bonding agents, allowing collapse and exclusion of the void space while simultaneously increasing intraurethral lumen space. The polymers may either spontaneously solidify or they may be polymerized or bound to the tissue upon exposure to an appropriate stimulus, as discussed in more detail below. The polymers are selected to facilitate healing, with minimal inflammatory and late fibrotic responses. Coordinating use of tissue friendly biodegradable polymeric bioadhesives insures frank volume reduction of the prostate as a result of closure and obliteration of cavities formed via direct tissue excision. Furthermore, the polymeric materials having drugs, genes or cells incorporated therein may serve as local depots for prolonged delivery of synergistic biochemical and cellular therapeutics, for example, to promote healing, decrease inflammation and/or collagen deposition and scarring, and manipulate endocrine processes and local growth control.

Alternatively, the void can be collapsed during surgery, for example, using suction or mechanical compression and/ or sutures or staples to close the opening, so that healing occurs primarily by adhesion. Means for collapsing the void (such as perforations to create suction or mechanical means for collapse or staples) can be included in the cutter, or multiple catheters used. Intraoperative prostate gland collapse will typically require a catheter or stent to hold open the urethra during this step.

Figure 6:
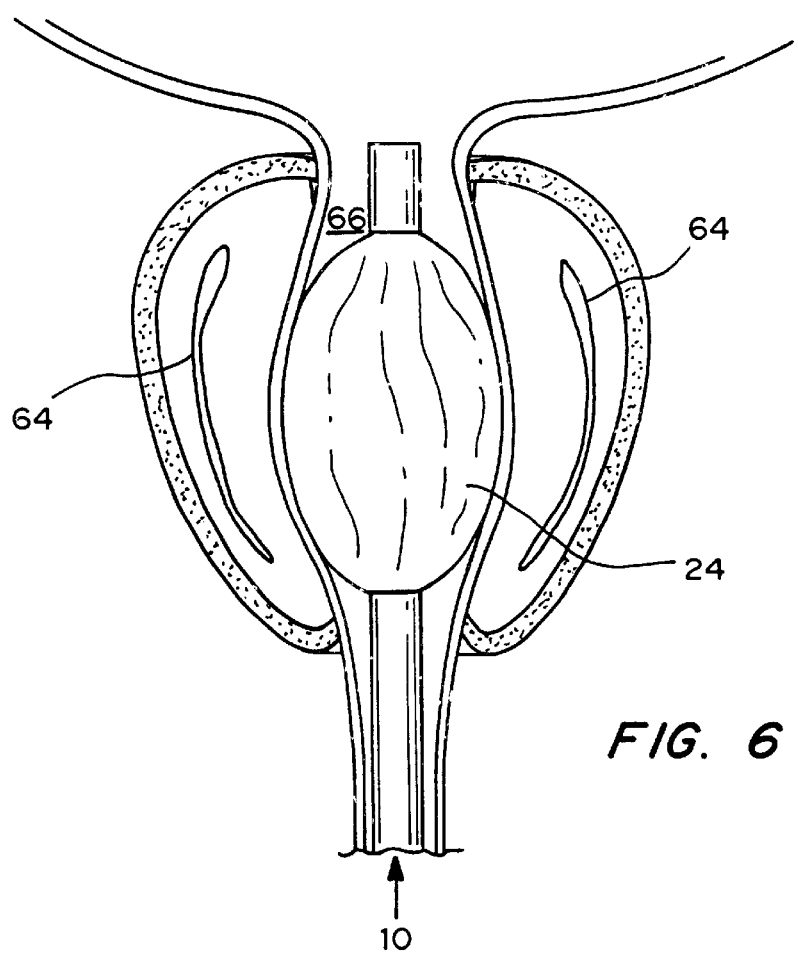
FIG. 6 is a schematic view of balloon reshaping of urethral volume.

After the polymeric adhesive is injected into the void, a balloon such as balloon 24 shown in FIG. 2, is inflated in the urethra 66 at the level of the prostate to collapse void 64, as shown in FIG. 6. The balloon 24 is shown after inflation and with the void 64 collapsed. The balloon may be kept inflated until the tissue adhesive bonds, excised tissue is squeezed out and/or until secondary bleeding is stopped.

A biodegradable polymeric liner (typically formed of a different polymer system than the adhesive) is then preferably placed within the lumen of the urethra to act as a wall support, maintaining urethral patency during healing, preventing patient discomfort and outflow obstruction. The liner may be applied through one of the lumens in the device 10 shown in FIG. 2. Balloon 24 can be used to press the liner against the urethral wall. Alternatively, there can be a completely separate supporting catheter used to apply and cure the polymeric liner in place.

The chemical and biological properties of the urethral liner inserted into the carved out void may vary, as discussed in more detail below. For example, the polymers can be infused in a particulate form, in a liquid carrier, or preformed as a solid but in a chopped form as a particle, flakes or fiber. It can be applied liberally to the tissue surface, where it can conform and/or penetrate the surface. This is then either heated or otherwise activated, for example, by exposure to light, preferably while continually applying pressure that expresses any residual fluid from the site of tissue removal within the prostate.

Figure 7A:
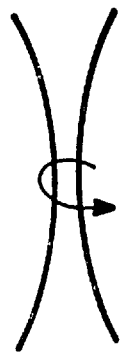
FIGS. 7A–7G are schematics of mechanical means for closure of voids created by the TUVOR process.
Figure 7B:
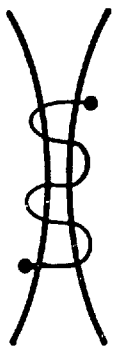
Figure 7C:
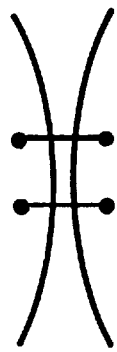
Figure 7D:
Figure 7E:
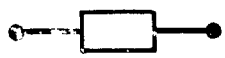
Figure 7F:
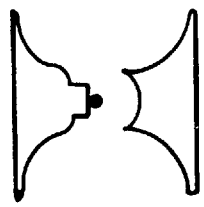
Figure 7G:
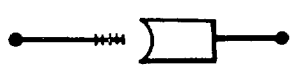

The adhesive polymeric material may be used to close the shelled out voids in the prostatic tissue alone or in combination with mechanical means. Mechanical means instead of an adhesive polymer can also be used. FIGS. 7A–7G are schematics of mechanical means for closure of voids created by the TUVOR process. FIG. 7A, localized sutures via endoluminal means; FIG. 7B, multiple sutures or weave; FIG. 7C, local staples or signlet closure means; FIG. 7D, linear tack-like closure means; FIG. 7E, closure means with central bolster element; FIG. 7F, button or snap closure system; and FIG. 7G, male-femal closure means.

The TUVOR device may also include a handle providing ergonomically located command switches, triggers, knobs and buttons through which all the TUVOR functions can be controlled. In addition there may be electrical means for actuating the rotating cutter. A power-supply means providing for both direct main and/or battery power can be included. Alternatively, pneumatic power may be used to power some features of the process.

Additional functions can be provided by a supporting console that integrates all necessary services such as: power supply, video processors, water-supply pumps, suction pumps, etc.

B. Polymeric or Hydrogel Materials

Biodegradable biocompatible materials are used to adhere the voids created by the cutter to enhance healing, to provide structural support within the urethra to assist or obviate the need for prolonged catheterization following surgery, and/or for drug delivery. For example, polymeric or hydrogel materials can be applied at the surface of or interior of cavities created by removal of tissue to treat the disorders caused by over proliferation or inflammation of tissue, such as the prostatic tissue. These materials can be used to adhere the sides of the tissue cavity together, to form a barrier at the surface of one or more of the tissue surfaces (to minimize inflammatory processes, for example), for delivery of bioactive agents, for the retention of radioisotopes, radiopaque particulate etc. The polymer may be deployed in the interior of the endomural tissue of the vessel or organ from the surface or tip of the catheter, as discussed above. Alternatively, the polymer can be applied by spraying, extruding or otherwise internally delivered via a long flexible tubular device consisting of as many lumens as a particular application may dictate.

Preferably, the method utilizes biodegradable or bioerodible synthetic or natural polymers, with specific degradation, lifespan and properties, which can be applied in custom designs, with varying thicknesses, lengths, and three-dimensional geometries (e.g. spot, stellate, linear, cylindrical, arcuate, spiral 8, etc.). The pharmaceutical delivery function of the process may be readily combined with the "customizable" deployment geometry capabilities to accommodate the interior of a myriad of complex organ or vessel surfaces. For example, polymer can be applied in either single or multiple polymer layer configurations and different pharmacological agents can be administered by application in different polymer layers when multiple polymer layers are used.

1. Selection of Polymeric Materials

A variety of different materials can be used, depending on the purpose, for example, structural, adhesive, barrier, or drug delivery. For those applications where structure is required, a polymer is selected which has appropriate mechanical and physical properties. It is preferred that the polymer be biodegradable over a period of time required to heal and form the tissue as desired according to the application. This may be a few days, weeks, or months. An advantage of the polymeric materials is that they can be tailored to shape the polymer into uneven surface interstices, while maintaining a smooth surface with good flow characteristics. Tissue narrowing, if it does occur, tends to stabilize beyond the six month window following the initial procedure without further accelerated narrowing. Optimally, if a foreign support device or sealant material is to be introduced into the tissue, it needs to exert its intended effect principally during the period of healing and peak inflammatory reaction. Although described herein principally with reference to polymeric materials, it is to be understood that other materials may also be used. For example, relatively low molecular weight organic compounds such as common sugars (e.g. sucrose), which are cast from concentrated, warm aqueous solution to set up as monolithic solids in situ and erode with minimal swelling or fragmentation may be used in place of a polymeric material. Inorganic compounds formed by ion exchange, such as polysilicic acid salts, degradable bioceramics, and "plasters" which degrade by surface erosion but which set in situ can also be used.

For those applications where the purpose does not require structural support properties, the polymer may be formed of a material that is bioadhesive, or impermeable to molecules of specified molecular weights, or highly permeable, releasing incorporating drug over a desired period of time, and consist of as little as a single layer of polymer.

Accordingly, the nature of the polymeric material used will be a function of whether it functions as a coating, bandage, adhesive, drug delivery device, or mechanical support role. Further, the choice of polymer must appropriately balance the degree of structural and geometric integrity needed against the appropriate rate of biodegradation over the time period targeted to prevent an undesirable reaction. In some cases, the material may be the same for different purposes where the ultimate in vivo geometry of the polymer dictates the final function of the polymer coating. The thinner applications allow the polymer film to function as a coating, sealant and/or partitioning barrier, bandage, and drug depot. Complex internal applications of thicker layers of polymer may actually provide increased structural support and, depending on the amount of polymer used in the layer, may actually serve in a mechanical role to maintain vessel or organ patency. For example, lesions which are comprised mostly of fibromuscular components have a high degree of visco-elastic recoil. These lesions require using the process to apply an endomural coating of greater thickness or stiffness and extent so as to impart more structural stability thereby resisting vessel radial compressive forces. This provides structural stability and is generally applicable for the maintenance of the intraluminary geometry of all tubular biological organs or substructure.

The basic requirements for the polymeric material are biocompatibility and the capacity to be applied in a solid or fluent state then chemically or physically reconfigured under conditions which can be achieved in vivo to yield a non-fluent polymeric material having defined characteristics in terms of mechanical strength, permeability, adhesion, and/or release of incorporated materials.

The polymeric materials can be applied as polymers, monomers, macromers or combinations thereof, maintained as solutions, suspensions, or dispersions, referred to herein jointly as "solutions" unless otherwise stated. Polymeric materials can be thermosettable, thermoplastic, polymerizable in response to free radical or ioin formation such as by photopolymerization, chemically or ionically crosslinkable (i.e., through the use of agents such as glutaraldehyde or ions like calcium ions). Examples of means of solidifying or polymerizing the polymeric materials including application of exogenous means, for example, application of light, ultrasound, radiation, or chelation, alone or in the presence of added catalyst, or by endogenous means, for example, a change to physiological pH, diffusion of calcium ions (e.g., alginate) or borate ions (e.g., polyvinyl alcohol) into the polymeric material, or change in temperature to body temperature (37° C.).

Although either non-biodegradable or biodegradable materials can be used, biodegradable materials are preferred. As used herein, "biodegradable" is intended to describe materials that are broken down into smaller units by hydrolysis, oxidative cleavage or enzymatic action under in vivo conditions, over a period typically less than one year, more typically less than a few months or weeks. For application to tissues to prevent inflammation, enlargement and/or over proliferation, it is preferred to use polymers degrading substantially within six months after implantation. For prevention of adhesions or controlled release, the time over which degradation occurs should be correlated with the time required for healing, i.e., generally in excess of two weeks but less than six months.

Suitable materials are commercially available or readily synthesizable using methods known to those skilled in the art. These materials include: soluble and insoluble, biodegradable and nonbiodegradable natural or synthetic polymers. These can be hydrogels or thermoplastics, homopolymers, copolymers or blends, natural or synthetic. As used herein, a hydrogel is defined as an aqueous phase with an interlaced polymeric component, preferably with 90% of its weight as water. The following definition is from the Dictionary of Chemical Terms, $4^{th}$ Ed., McGraw Hill (1989): Hydrogel: a colloid in which the disperse phase (colloid) has combined with the continuous phase (water) to produce a viscous jellylike product, for example, coagulated silicic acid. An organogel is defined as an organic phase with an interlaced polymeric component, preferably with 90% of its weight as organic solvent. Preferred solvents include non-toxic organic solvents, such as dimethyl sulfoxide (DMSO), and mineral and vegetable oils. The preferred polymers are synthetic polymers, formable or synthesizable in situ, with controlled synthesis and degradation characteristics.

Representative Polymeric Materials for direct application to tissue.

Representative natural polymers include proteins, such as zein, modified zein, casein, gelatin, gluten, serum albumin, or collagen, and polysaccharides, such as cellulose, dextrans, hyaluronic acid, polymers of acrylic and methacrylic esters and alginic acid. These are not preferred due to higher levels of variability in the characteristics of the final products, as well as in degradation following administration. Synthetically modified natural polymers include alkyl celluloses, hydroxyalkyl celluloses, cellulose ethers, cellulose esters, and nitrocelluloses, acylic or mrthacrylic esters of above natural polymers to introduce unsaturation into the biopolymers.

Representative synthetic polymers include polyesters, polyphosphazines, poly(vinyl alcohols), polyamides, polycarbonates, polyalkylenes, polyacrylamides, polyalkylene glycols, polyalkylene oxides, polyalkylene terephthalates, polyvinyl ethers, polyvinyl esters, polyvinyl halides, polyvinylpyrrolidone, polysiloxanes, polyurethanes and copolymers thereof. Other polymers include celluloses such as methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxymethyl cellulose, cellulose triacetate, cellulose sulfate sodium salt, acrylates such as poly(methyl methacrylate), poly(ethyl methacrylate), poly(butyl methacrylate), poly (hexyl methacrylate), poly(isodecyl methacrylate), poly (lauryl methacrylate), poly(phenyl methacrylate), poly (methyl acrylate), poly(isopropyl acrylate), poly(isobutyl acrylate), poly(octadecyl acrylate), polyethylene, polypropylene, poly(ethylene glycol), poly(ethylene oxide), poly(vinyl acetate), polyvinyl chloride, polystyrene, polyvinyl pyrrolidone, and polyvinylphenol. Representative bioerodible polymers include polylactides, polyglycolides and copolymers thereof, poly(hydroxy butyric acid), poly (hydroxyvaleric acid), poly(lactide-cocaprolactone), poly [lactide-co-glycolide], polyanhydrides, polyorthoesters, blends and copolymers thereof.

These polymers can be obtained from sources such as Sigma Chemical Co., St. Louis, Mo., Polysciences, Warrenton, Pa., Aldrich, Milwaukee, Wis., Fluka, Ronkonkoma, N.Y., and BioRad, Richmond, Calif. or else synthesized from monomers obtained from these suppliers using standard techniques.

These materials can be further categorized as follows.
Materials which Polymerize or Alter Viscosity as a Function of Temperature.

Poly(oxyalkene) polymers and copolymers such as poly (ethylene oxide)poly(propylene oxide) (PEO-PPO) copolymers, and copolymers and blends of these polymers with polymers such as poly(alpha-hydroxy acids), including but not limited to lactic, glycolic and hydroxybutyric acids, polycaprolactones, and polyvalerolactones, can be synthesized or commercially obtained. For example, polyoxyalkylene copolymers are described by U.S. Pat. Nos. 3,829,506; 3,535,307; 3,036,118; 2,979,578; 2,677,700; and 2,675,619, the teachings of which are incorporated herein. Polyoxyalkylene copolymers are sold by BASF and others under the tradename Pluronic™. Preferred materials include F-27, F-108, and for mixtures with other gel materials, F-67. These materials are applied as viscous solutions at room temperature or lower which solidify at the higher body temperature. Another example is a low Tm and low Tg grade of styrene-butadiene-styrene block copolymer from Polymer Concept Technologies, C-flex™. Polymer solutions that are liquid at an elevated temperature but solid at body temperature can also be utilized. For example, thermosetting biodegradable polymers for in vivo use are described in U.S. Pat. No. 4,938,763 to Dunn, et al.

Materials which Polymerize in the Presence of Multivalent Ions.

Several divalent ions including calcium, barium, magnesium, copper, and iron are normal constitutents of the body tissues and blood. These ions can be used to ionically crosslink polymers such as the naturally occurring polymers collagen, fibrin, elastin, agarose, agar, polysaccharides such as hyaluronic acid, hyalobiuronic acid, heparin, cellulose, alginate, curdlan, chitin, and chitosan, and derivatives thereof cellulose acetate, carboxymethyl cellulose, hydroxymethyl cellulose, cellulose sulfate sodium salt, and ethylcellulose.

Materials that can be Crosslinked Photochemically, with Ultrasound or with Radiation.

Materials that can be crosslinked using light, ultrasound or radiation will generally be those materials which contain a double bond or triple bond, preferably with an electron withdrawing substituent attached to the double or triple bond. Examples of suitable materials include the monomers which are polymerized into poly(acrylic acids) (i.e., Carbopols.™.), poly(acrylates), polyacrylamides, polyvinyl alcohols, acrylated polyethylene glycols, and ethylene vinyl acetates. Photopolymerization requires the presence of a photosensitizer, photoinitiator or both, any substance that either increases the rate of photoinitiated polymerization or shifts the wavelength at which polymerization occurs. The radiolysis of olefinic monomers results in the formation of cations, anions, and free radicals, all of which initiate chain polymerization, grafting and crosslinking and can be used to polymerize the same monomers as with photopolymerization. Photopolymerization can also be triggered by applying appropriate wavelength to a cyclo-dimerizable systems such as Coumarin and Cinnamic acid derivatives. Alpha-hydroxy acids backbone can be activated to carbonium ion. COOH or $SO_3H$ functionality can be inserted that can be subsequently reacted to amine containing ligands Materials that can be Crosslinked by Addition of Covalent Crosslinking Agents such as Glutaraldehyde.

Any amino containing polymer can be covalently crosslinked using a dialdehyde such as glutaraldehyde, or succindialdehyde. Examples of useful amino containing polymers include polypeptides and proteins such as albumin, and polyethyleneimine. Peptides having specialized function, as described below, can also be covalently bound to these materials, for example, using crosslinking agents, during polymerization.

Enhancement of Muco or Tissue Adhesive Properties of Polymeric Materials

Polymers with free carboxylic acid or other anionic groups (e.g., sulfonic acid), such as the acrylic acid polymers noted above, can be used alone or added to other polymeric formulations to enhance tissue adhesiveness. Alternatively, materials that have tissue binding properties can be added to or bound to the polymeric material. Peptides with tissue adhesion properties are discussed below. Lectins that can be covalently attached to a polymeric material to render it target specific to the mucin and mucosal cell layer could be used. Useful lectin ligands include lectins isolated from: *Abrus precatroius, Agaricus bisporus, Anguilla anguilla, Arachis hypogaea, Pandeiraea simplicifolia, Bauhinia purpurea, Caragan arobrescens, Cicer arietinum, Codium fragile, Datura stramonium, Dolichos biflorus, Erythrina corallodendron, Erythrina cristagalli, Euonymus europaeus, Glycine max, Helix aspersa, Helix pomatia, Lathyrus odoratus, Lens culinaris, Limulus polyphemus, Lysopersicon esculentum, Maclura pomifera, Momordica charantia, Mycoplasma gallisepticum, Naja mocambique*, as well as the lectins Concanavalin A, Succinyl-Concanavalin A, *Triticum vulgaris, Ulex europaeus* I, II and III, *Sambucus nigra, Maackia amurensis, Limaxfluvus, Homarus americanus, Cancer antennarius*, and *Lotus tetragonolobus*.

The attachment of any positively charged ligand, such as polyethyleneimine, polylysine or chitosan to any microsphere or polymeric chain may improve bioadhesion due to the electrostatic attraction of the cationic groups to the net negative charge of the mucus. A surfactant-like molecule bearing positive charge and a hydrophobic core would be comaptible with the bilayer membrane. This molecule will distribute its core and the positive charge to minimize energy of interaction and hence will be more tissue adhesive.The mucopolysaccharides and mucoproteins of the mucin layer, especially the sialic acid residues, are responsible for the negatively charged surface layer. Any ligand with a high binding affinity for mucin could also be covalently linked to the polymeric material.

Polymeric materials can also be used as tissue adhesives. In one form, fibrin is used. This has the advantage that it can be formed easily in situ using the patient's own fibrinogen, blood or serum, by addition of thrombin and calcium chloride. The materials described above can also be used. Other polymeric tissue adhesives that are commercially available include cyanoacrylate glues, GRF (Gelatin-resorcinol-formaldehyde) and polyethyleneglycol-poly(lactic acid and/or glycolic acid)-acrylates, both of which are applied as liquids and then photopolymerized.

Manipulation of Physical Properties of Polymeric Materials

The polymeric material can be designed to achieve a controlled permeability, either for control of materials within the cavity or into the tissue or for release of incorporated materials. There are basically three situations that the polymeric material is designed to achieve with respect to materials present in the lumen: wherein there is essentially passage of only nutrients (small molecular weight compounds) and gases from the lumen through the polymeric material to the tissue lumen surface; wherein there is passage of nutrients, gases and macromolecules, including large proteins and most peptides; and wherein there is passage of nutrients, gases, macromolecules and cells. The molecular weight ranges of these materials are known and can therefore be used to calculate the desired porosity. For example, a macromolecule can be defined as having a molecular weight of greater than 1000 daltons; cells generally range from 600–700 nm to 10 microns, with aggregates of 30–40 microns in size. For passage of cell, the material must possess or develop a macroporous structure.

Formation of Materials which have Decreased Volume Following Polymerization

Under certain circumstances it may be useful to produce a polymer in situ which occupies a smaller volume than the solution from which it is applied, for example, as an adhesive for the prostate gland to hold the walls together. The polymerization can be accompanied by "syneresis" or expulsion of water from the polymer, during polymerization. Besides reducing mass of the product, this process may yield porous products which may be desirable for healing. Syneresis occurs when a polymerization reaction occurs with reaction of a large number of fractional groups per unit volume (high crosslinking density or when dilute solutions of reactants are polymerized and the amount of water in the formulation exceeds the intrinsic swelling capacity of the resulting polymer. The latter may occur, for example, when dilute solutions of PEG-diacrylate are polymerized (e.g., less than or equal to 5% macromer).

Incorporation of Bioactive Agents

A wide variety of bioactive agents can be incorporated into the polymeric material. These can be physically incorporated or chemically incorporated into the polymeric material. Release of the physically incorporated material is achieved by diffusion and/or degradation of the polymeric material; release of the chemically incorporated material is achieved by degradation of the polymer or of a chemical link coupling the bioactive material to the polymer, for example, a peptide which is cleaved in vivo by an enzyme such as trypsin, thrombin or collagenase. In some cases, it may be desirable for the bioactive agent to remain associated with the polymeric material permanently or for an extended period, until after the polymeric material has degraded and removed from the site. In the broadest sense, the bioactive materials can include proteins (as defined herein, including peptides generally construed to consist of less than 100 amino acids unless otherwise specified), saccharides, polysaccharides and carbohydrates, nucleic acids, and synthetic organic and inorganic materials, or combinations thereof.

Specific materials include antibiotics, antivirals, antiinflammatories, both steroidal and non-steroidal, antineoplastics, anti-spasmodics including channel blockers, modulators of cell-extracellular matrix interactions including cell growth inhibitors and anti-adhesion molecules, enzymes and enzyme inhibitors, anticoagulants, growth factors, DNA, RNA and protein synthesis inhibitors, anti-cell migratory agents, vasodilating agents, and other drugs commonly used for the treatment of injury to tissue. Examples of these compounds include angiotensin converting enzyme inhibitors, anti-thrombotic agents, prostacyclin, heparin, salicylates, thrombolytic agents, anti-proliferative agents, nitrates, calcium channel blocking drugs, streptokinase, urokinase, tissue plasminogen activator (TPA) and anisoylated plasminogen activator (TPA) and anisoylated plasminogen-streptokinase activator complex (APSAC), GPIIb/IIIA antagonists, colchicine and alkylating agents, growth modulating factors such as interleukins, transformation growth factor .beta. and congeners of platelet derived growth factor, fibroblast growth factor, epidermal growth factor, hepatocyte scatter factor, monoclonal antibodies directed against growth factors, modified extracellular matrix components or their receptors, lipid and cholesterol sequestrants, matrix metalloproteases (MMPs), collagenase, plasmin and other agents which may modulate tissue tone, function, and the healing response to organ injury post intervention. Additional examples of such compounds include nitric oxide containing, releasing or producing materials, antiproliferatives as well as antioxidants, a number of which are known.

Hormones, especially reproductive or sex homones, may be particularly advantageous to deliver using these materials. It may also be useful to deliver chemotherapeutics such as BCNU, cisplatin, taxol, and other cytotoxic agents. Materials such as attachment peptides (such as the FN cell-binding tetrapeptide Arg-Gly-Asp-Ser (RGDS)), selectin receptors and carbohydrate molecules such as Sialyl Le.sup.x, can be used which serve to attract and bind specific cell types, such as white cells and platelets. Materials such as fibronectin, vimentin, and collagen, can be used to non-specifically bind cell types, to enhance healing. Other proteins known to carry functional RGD sequences include the platelet adhesion proteins fibrinogen, vitronectin and von Willebrand factor, osteopontin, and laminin. Specific RGD peptides are described in U.S. Pat. No. 4,517,686 to Ruoslahti, et al., U.S. Pat. No. 4,589,881 to Pierschbacher, et al., U.S. Pat. No. 5,169,930 to Ruoslahti, et al., U.S. Pat. No. 5,149,780 to Plow, et al., U.S. Pat. No. 4,578,079 to Ruoslahti, et al., U.S. Pat. No. 5,041,380 to Ruoslahti, et al., and Pierschbacher and Ruoslahti, *J. Biol. Chem.* 262(36), 17294–17298 (1987), Mohri, et al., *Amer. J. Hem.* 37:14–19 (1991), Aumailley, et al., FEBS 291(1), 50–54 (1991), Gurrath, et al., *Eur. J. Biochem.* 210, 911–921 (1992), and Scarborough, et al., *J. Biol. Chem.* 268(2), 1066–1073 (1993). Laminin promotes cell adhesion, migration, differentiation, and growth (Kleinman, et al., *J. Cell Biochem.* 27:317–325 (1985); Kleinman, et al., *Biochem.* 25:312–318 (1986); Beck, et al., *FASEB J.* 4:148–160 (1990). The nonapeptide CDPYIGSR promotes cell attachment and migration (Graf, et al., *Cell* 48:989–996 (1987), *Biochem.* 26:6896–6900 (1987)). Further studies have shown that YIGSR-containing peptides can inhibit angiogenesis and tumor metastasis (Grant, et al., *Cell* 58:933–943 (1989), Iwamoto, et al., *Science* 238:1132–1134 (1987), Sakamoto, et al., *Cancer Res.* 51:903–906 (1991). Other peptides include PDSGR and IKVAV. Integrins typically bind to cell adhesion proteins via the rather highly conserved sequence Arg-Gly-Asp X (RGDX), where X is variant depending on the particular cell adhesion protein.

Cells can also be incorporated in the material. Cells to be incorporated include prostatic stromal cells and/or fibroblasts or other mesenchymal cells to facilitate closure of tissue voids. Altemativley glandular epithelial cells, either mature, developing, embryonic/fetal or genetically engineered, may be deposited. These may serve to alter regional or systemic physiology through endocrine or paracrine hormone or other mediator release.

In most cases, it is possible to physically incorporate the bioactive agent by mixing it with the material prior to application to the tissue surface or within the cavity and polymerization or solidification. The material can be mixed into the monomer solution to form a solution, suspension or dispersion. In another embodiment, the bioactive agent can be encapsulated within delivery devices such as microspheres, microcapsules, liposomes, cell ghosts or psuedovirions, which in themselves affect release rates and uptake by cells such as phagocytic cells.

Bioactive agents can be chemically coupled (conjugated) to the polymeric material, before or at the time of polymerization. Bioactive materials can also be applied to the surface of stents or catheters used in the procedures described herein, alone or in combination with the polymeric materials. Catheter and other device or implant bodies are made of standard materials, including metals such as surgical steel and thermoplastic polymers. Occluding balloons may be made from compliant materials such as latex or silicone, or non-compliant materials such as polyethylene terephthalate (PET). The expansible member is preferably made from non-compliant materials such as PET, (PVC), polyethylene or nylon. The balloon catheter portion may optionally be coated with materials such as silicones, polytetrafluoroethylene (PTFE), hydrophilic materials like hydrated hydrogels and other lubricous materials to aid in separation of the polymer coating.

Several polymeric biocompatible materials are amenable to surface modification in which surface bound bioactive molecules/ligands exhibit cellular binding properties. These methods are described by Tay, Merrill, Salzman and Lindon in Biomaterials 10, 11–15 (1989), the teachings of which are incorporated herein by reference.

Covalent linkages can be formed by reacting the anhydride or acid halide form of an N-protected amino acid, poly(amino acid) (two to ten amino acids), peptide (greater than 10 to 100 amino acids), or protein with a hydroxyl, thiol, or amine group on a polymer. The amine groups on the amino acid or peptide must be protected before forming the acid halide or anhydride, to prevent selfcondensation. N-protection is well known by those skilled in the art, and can be accomplished by use of various protecting groups, such as a carbobenzoxy (CBZ) group.

The term "protecting group" as used herein refers to a moeity which blocks a functional group from reaction, and which is cleavable when there is no longer a need to protect the functional group. Examples of functional groups include, but are not limited to, amino, hydroxy, thio, and carboxylate groups. Examples of protecting groups are well known to those skilled in the art.

A carboxyl-containing compound can contain various functional groups, such as hydroxy, thio, and amino groups, that can react with an acid halide or anhydride. These functional groups must be protected before forming an acid chloride or anhydride to avoid self-condensation. After formation of the acid chloride or anhydride, and subsequent reaction with the hydroxyl, thiol, or amino group(s) on another molecule, the protecting group can be removed in a "deprotecting" step. The N-protected amino groups can be deprotected by means known to those skilled in the art. Any hydroxy or thio groups on these compounds must be protected so as not to react with the acid halides or anhydrides. Examples of suitable protecting groups for alcohols include but are not limited to trialkyl silyl groups, benzyl ethers, and tetrahydropyranyl ethers. These groups can be protected by means known to those skilled in the art, and can be subsequently deprotected after the esterification is complete. Examples of protecting groups can be found in Greene, T. W., and Wuts., P; G. M., "Protective Groups in Organic Synthesis 2d Ed., John Wiley & Sons, Inc., pp. 317–318 (1991), hereby incorporated by reference.

A method for preparation of acid halide derivatives is to react the carboxylic acid with thionyl chloride, preferably in benzene or toluene with a catalytic amount of DMF. A known method for producing anhydrides is to react the carboxylic acid with acetic anhydride. In this reaction, as acetic acid is formed, it is distilled out of the reaction vessel. Peptides can be covalently bound to the polymeric material, for example, when the polymeric material is a polymer of an alpha hydroxy acid such as poly(lactic acid), by protecting the amine functionality on the peptide, forming an acid halide or anhydride of the acid portion of the polymer, reacting the acid halide or anhydride with free hydoxy, thiol, or amine groups on the polymer, then deprotecting the amine groups on the peptide to yield polymer having peptide bound thereto via esterification, thioesterification, or amidation. The peptide can also be bound to the polymer via a free amine using reductive amination with a dialdehyde such as glutaraldehyde.

The ester groups on a polyester surface can be hydrolyzed to give active hydroxy and carboxyl groups. These groups can be used to couple bioactive molecules. Preferably, before converting the active carboxylate group to the acid halide or anhydride form, the active hydroxy group is protected to avoid reaction with the resulting acid halide or anhydride. As a non-limiting example, the active hydroxy group can be protected as a benzyl ether. The active carboxyl group can then be converted to the acid halide or anhydride, and reacted with a hydroxy or amino group on a second compound to form an ester or amide linkage. The O-protected hydroxy group can then be deprotected.

Polyanhydrides can be partially hydrolyzed to provide carboxyl groups. The resulting carboxyl groups can be converted to acid halides, which can be reacted with amino acids, peptides, or other amine containing compounds with binding properties and form an amide linkage.

Polyesters and polylactones can be partially hydrolyzed to free hydroxyl and carboxyl groups. The hydroxyl groups can be protected by means known to those skilled in the art, and the carboxyl groups converted to acid halides. The acid halides can be reacted with amino acids, peptides, or other amine containing compounds with binding properties and form an amide linkage. Alternatively, if the hydroxyl groups are primary or secondary hydroxyl groups, they can be oxidized to aldehydes or ketones, and reacted with amines via reductive amination to form a covalent linkage.

Polyamides can be partially hydrolyzed to provide free amine and carboxylic acid groups. The amine group can then be reacted with an amino acid or peptide in which the amine groups have been protected, and the carboxyl groups have been converted to acid halides. Alternatively, the amine groups on the polyamide can be protected, and the carboxyl groups converted to acid halides. The resulting acid halides can then be reacted directly with the amine groups on amino acids or peptides.

Polyethers with terminal hydroxy groups can be appended with amino acids or peptides. One first protects the amine groups, then converts the carboxyl groups on the amino acid or peptide to acid halides. The acid halide can be reacted directly with the hydroxy group to provide an ester linkage.

The acid halides described above can also be reacted with thiol groups to form thioesters.

Coupling agents such as carbodiimides, diisocyanates, or organosilanes can be used to bind polymers, or metals and ceramics to bioactive agents covalently. For example, a metal stent may be treated with an aqueous solution of an aminotrialkoxy silane. These form an amino functional surface which can react with carboxy-functional proteins, for durable attachment or controlled release. Carbodiimides can react with carboxyl functional groups to produce amino-reactive intermediates. Carboxy functional polymers can be reacted to form N-hydroxy succinimide esters which are very reactive with amino groups on peptides. This chemistry has been used to form surgical sealants PEG-di-N-hydroxysuccinimide and albumin, Barrows, et al., 3M Corporation, but could be used to couple bioactive molecules to polymers.

2. Application of Polymeric Materials

In general terms, the polymeric material is a biocompatible polymeric material having a variable degree of fluency in response to a stimulus or mechanical pressure, as described above. The material is such that it is substantially non-fluent in vivo upon completion of the coating process. The material, in its fluent form or a conformable form, is positioned in contact with a tissue or device surface to be coated and then stimulated to render it non-fluent or conformed, as described above. The polymeric material is applied to the cavity created by the TUVOR process and/or the urethral lumen lining using catheters, syringes, or sprays, depending on the tissue surface or device to which it is applied, using the devices described above or devices known to those skilled in the art.

The coating typically will be applied to the tissue surface such as the urethra using some type of catheter. The coating material is preferably applied using a single catheter with single or multiple lumens. The catheter should be of relatively low cross-sectional area. A long thin tubular catheter manipulated using endoscopic guidance is preferred for providing access to the interior of organ areas.

Application of the coating material may be accomplished by extruding a solution, dispersion, or suspension of monomers, polymers, macromers, or combinations thereof through a catheter to coat or fill a tissue surface or cavity, then controlling formation of the coating by introducing crosslinking agents, gelling agents or crosslinking catalysts together with the fluent material and then altering the conditions such that crosslinking and/or gelling occurs. Thus, when a balloon catheter is used, a flow of heated or chilled fluid into the balloon can alter the local temperature to a level at which gelling or cross-linking is induced, thereby rendering the material non-fluent. Localized heating or cooling can be enhanced by providing a flow of heated or chilled liquid directly onto the treatment site. Thermal control can also be provided, however, using a fluid flow through or into the balloon, or using a partially perforated balloon such that temperature control fluid passes through the balloon into the lumen. Thermal control can also be provided using electrical resistance heating via a wire running along the length of the catheter body in contact with resistive heating elements. This type of heating element can make use of DC or radio frequency (RF) current or external RF or microwave radiation. Other methods of achieving temperature control can also be used, including light-induced heating using an internal optical fiber (naked or lensed). The polymer formulation can contain components which convert light into heat energy. Similar devices can be used for application of light, ultrasound, or irradiation.

Any of the foregoing materials can be mixed with other materials to improve their physiological compatibility. These materials include buffers, physiological salts, conventional thickeners or viscosity modifying agents, fillers such as silica and cellulosics, and other known additives of similar function, depending on the specific tissue to which the material is to be applied.

The process of fixing the shape of the polymeric material can be accomplished in several ways, depending on the character of the original polymeric material. For example, a partially polymerized material can be expanded using a balloon after which the conditions are adjusted such that polymerization can be completed, e.g., by increasing the local temperature or providing UV or visible radiation through an optical fiber. A temperature increase might also be used to soften a fully polymerized sleeve to allow expansion and facile reconfiguration and local molding, after which it would "freeze" in the expanded position when the head source is removed. Of course, if the polymeric sleeve is a plastic material which will permanently deform upon stretching (e.g., polyethylene, polyethylene terephthalate, nylon or polyvinyl chloride), no special fixation procedure is required.

The present invention will be further understood by reference to the following non-limiting examples.

EXAMPLE 1

Application of a Polymeric Lining on the Urethral Lumen Following the TUVOR Procedure An incision in the prostatic adenoma mass is made and a specific volume of the tumor is excised. A variety of different polymeric materials can then be applied into this incision to prevent closure and provide for drug delivery. A tissue adhesive can also be administered to close the wound created by removal of the prostatic tissue.

The following are examples of polymeric materials that can be used to line the urethra and/or the cavity within the prostate.

1. Administration of a Thermoplastic Polymeric Coating.

Poly(caprolactone) (PCL) polymer (PCL has Tm=less than 60° C. and Tg=60° C.) and a low Tm and low Tg grade of styrene-butadiene-styrene block copolymer from Polymer Concept Technologies, C-flex™, were cryogenically ground to form particulates not greater than 50 micron. 5 g of the ground PCL powder was mixed with 2 g of 25% Pluronic™ (F-127) solution in PBS. 0.02 g of Triton™ surfactant was added to stabilize the suspension.

The final suspension is applied endoscopically to the urethral lumen area by a deploying device. The device is equipped with an infrared source. Following the application of the suspension the infrared source is fired and held in place for 30 seconds. This results in a PCL coated urothelial lumen with intermittent irrigation of PBS.

In another embodiment, the same suspension is used and same procedure is implemented except that the deploying device has a saline firing system that will irrigate the area of the urothelium during the deployment period of PCL. This will reduce the tissue damage from hyperthennia.

2. Administration of Mucoadhesive Polymeric Coating.

Polymers or other materials with mucoadhesive properties, such as polymers with available carboxylic groups, can be used. For example, polyacrylic acid (PAA) can be added to the polymer suspension described above to obtain a final concentration of 5% w/w in the Pluronic™ suspension.

3. Application of a Polymeric Coatingformed by Chemical Crosslinking.

Alternatively, crosslinking agents can be used with the polymer. An example of such a system is a gelatin-resorcin-formaldehyde (GRF) system. Other crosslinking agents which can be used include glutaraldehyde and ethanedial.

a. A 10% w/w Gelatin solution is made in PBS. Resorcin is added to this solution such that the final solution concentration of resorcin is 3% w/w. A 2% w/w crosslinking solution of formaldehyde is made in PBS separately. C-flex™ polymer is cryogenically ground to form particulates not greater than 50 microns in diameter. 5 g of ground C-flex™ powder is mixed with 2 g of the gelatin-Resorcin solution. 0.01 g of Triton™ surfactant is added to stabilize the suspension.

The final suspension is applied endoscopically to the urethral lumen area by a deploying device. The device is equipped with a infra-red light source. The crosslinking solution is added and simultaneously the infra-red source is fired. This initiates crosslinking of the matrix and melting of the polymer at the same time to yield a C-flex™ coated urothelial lining.

b. A 10% w/w Gelatin solution is made in PBS. Resorcin is added to this solution such that the final solution concentration of resorcin is 3% w/w. A 2% w/w crosslinking solution of formaldehyde and glutaraldehyde (1:1 weight ratio) is made in PBS separately. PCL polymer is cryogenically ground to form particulates not greater than 50 micron. 5 g of ground PCL powder is mixed with 2 g of the gelatin-Resorcin solution. 0.02 g of Triton™ surfactant is added to stabilize the suspension.

The final suspension is applied endoscopically to the urethral lumen area by a deploying device equipped with a infrared light source. The crosslinking solution is added and simultaneously the infrared source is fired. This initiates crosslinking of the matrix and melting of the polymer at the same time to produce a PCL coated urothelial lining.

c. A 10% w/w Gelatin solution is made in PBS. Resorcin is added to this solution such that the final solution concentration of resorcin is 3% w/w. A 2% w/w crosslinking solution of pentandial and ethanedial (1:1 weight ratio) is made in PBS separately. C-flex™ polymer is cryogenically ground to form particulates not greater than 50 microns. 5 g of ground C-flex™ powder is mixed with 2 g of the gelatin-Resorcin solution. 0.02 g of Triton™ surfactant is added to stabilize the suspension.

The final suspension is applied endoscopically to the urethral lumen area by a deploying device equipped with a infra-red light source. The crosslinking solution is added and simultaneously the infra-red source is fired. This initiated crosslinking of the matrix and melting of the polymer at the same time to yield a C-flex™ coated urothelial lining.

4. Application of Photopolymerizable Polymeric Coating.

a. Gelatin-poly(L=Glutamic acid) reacted with water soluble carbodiimide (WSC), photoactivatable Gelatin (benzophenone conjugated gelatin, which acts as the photoinitiator), and PEG-DA as carrier gel for the C-flex™ system.

b. A 10% w/w benzophenone conjugated-Gelatin solution is made in PBS. Polyethylene glycol - diacrylate (PEG-DA) (MW 600) is added to the solution to achieve a final concentration of 15% w/w solution in PBS. PCL polymer is cryogenically ground to form particulates not greater than 50 microns. 5 g of ground PCL powder is mixed with 2 g of the gelatin-PEG-DA solution. 0.02 g of Triton™ surfactant is added to stabilize the suspension.

The final suspension is applied endoscopically to the urethral lumen area by a deploying device. The device is equipped with a long-wave UV light. Following the application of the suspension the UV source is fired and held in place for 30 seconds to induce the crosslinking of the matrix and the heat absorbed from the UV source softens the polymer to form a conformal coating along the urothelium. The tissue adhesive property of the matrix gel will enhance the performance of the polymer during the deployment stage.

c. A 10% w/w benzophenone conjugated-Gelatin solution is made in PBS. PEG-DA is added to the solution to achieve a final concentration of 25% w/w solution in PBS. C-flex™ polymer is cryogenically ground to form particulates not greater than 50 micron. 5 g of ground C-flex™ powder is mixed with 2 g of the gelatin-PEG-DA solution. 0.02 g of Triton surfactant is added to stabilize the suspension.

The final suspension is applied endoscopically to the urethral lumen area by a deploying device equipped with a long-wave UV light. Following the application of the suspension, the uv source is fired and held in place for 30 seconds. This induces crosslinking of the matrix and the heat absorbed from the uv source softens the polymer to form a conformal coating along the urothelium. The tissue adhesive property of the matrix gel enhances the performance of the polymer during the deployment stage.

d. In another embodiment, a 10% w/w eosin-Y conjugated-Gelatin solution is made in PBS. PEG-DA (MW 600) is added to the solution to achieve a final concentration of 25% w/w solution in PBS. C-flex™ polymer is cryogenically ground to form particulates not greater than 50 micron. 5 g of ground C-flex™ powder is mixed with 2 g of the gelatin-PEG-DA solution. 0.02 g of Triton™ surfactant is added to stabilize the suspension.

The final suspension is applied endoscopically to the urethral lumen area by a deploying device equipped with a visible wavelength source. Following the application of the suspension the visible light source is fired and held in place for 30 seconds. This induces crosslinking of the matrix and the heat absorbed from the uv source softens the polymer to form a conformal coating along the urothelium. The tissue adhesive property of the matrix gel enhances the performance of the polymer during the deployment stage.

EXAMPLE 2

Application of Tissue Adhesive in the Cavity Created in the Tumor by the Tumor Volume Reduction Technique (TUVOR).

An incision in the prostatic tumor mass is made and a specific volume of the tumor is excised as described in example 1. A tissue adhesive is then applied within the cavity to enhance healing of the wound. The following are examples of useful tissue adhesives to close the voids in the prostatic masses.

a. 1 gm of 50 mg Fibrinogen/ml is mixed in situ with 0.3 g of 150 NIH U thrombin/ml containing 100 mM $CaCl_2$ at the site of the cavity. This forms a tissue glue within 90 sec.

b. 2 gm of 100 mg Fibrinogen/ml is mixed in situ with 0.3 g of 150 NIH U thrombin/ml containing 100 mM $CaCl_2$ at the site of the cavity. This forms a tissue glue within 30 sec.

c. 1 gm of 50 mg Fibrinogen/ml is supplemented with 2500 kIU Aprotinin/ml with 12.5 mg epsilon-aminocaproic acid/ml. The solution is mixed in situ with 0.3 g of 150 NIH U thrombin/ml containing 100 mM $CaCl_2$ at the site of the cavity. This will delay the in vivo degradation of Fibrin glue and retain the collapsed state of the cavity for a longer duration of time. Tranexamic acid can be used instead of aprotinin for better healing response of the tissue. In another example, the cavity created by the TUVOR technique is aspirated following washing with a concentrated ethanol solution (80% w/w in water). This process dehydrates the local area of the cavity. The in situ Fibrin glue is applied as described above to promote better adhesion of the tissue.

Modifications and variations of the methods and compositions described above will be obvious to those skilled in the art and are intended to be encompassed by the following claims.

We claim:

1. A method for treating prostate disease comprising:
making an incision into the prostate,
reducing the volume of the prostate by removing endomural tissue to form at least one void in the prostate, and
closing the voids in the prostate,
wherein an adhesive material is applied within the void prior to closure or a supportive material is applied to the urethra lining to provide structural support.

2. The method of claim 1 comprising applying an adhesive biodegradable material within the voids prior to closure.

3. The method of claim 2 wherein the adhesive biodegradable material is sufficient to effect closure of the voids until healing occurs.

4. The method of claim 1 wherein the voids are closed by mechanical means.

5. The method of claim 4 wherein the voids are closed using a balloon catheter within the urethra.

6. The method of claim 1 wherein the incision is a transurethral incision.

7. The method of claim 1 wherein multiple voids are created in the prostate.

8. The method of claim 1 wherein the incision and tissue removal is effected using a cutter device positioned within a catheter that can be passed into the urethra to the prostate.

9. The method of claim 1 further comprising administering bioactive agents to the urethra or voids within the prostate.

10. The method of claim 9 wherein the bioactive agents are selected from the group consisting of drugs, genes, cells, and molecules altering cellular adhesion.

11. The method of claim 10 wherein the drugs are selected from the group consisting of antibiotics, antivirals, antiinflammatories, hormones, antineoplastics, antispasmodics, modulators of cell-extracellular matrix interactions, enzymes, enzyme inhibitors, anticoagulants, growth factors, DNA, RNA and protein synthesis inhibitors, anti-cell migratory agents, and vasodilating agents.

12. The method of claim 11 wherein the drugs are selected from the group consisting of hormones and chemotherapeutic agents.

13. The method of claim 1 wherein the material applied to the urethra lining provides structural support sufficient to allow flow of urine through the urethra.

14. The method of claim 1 wherein material applied to the voids or urethra lining is a polymer.

15. The method of claim 14 wherein the polymer is a biodegradable polymer.

16. The method of claim 15 wherein the polymer is conformable by a change in temperature or mechanical forces in situ.

17. The method of claim 15 wherein the polymer is applied in a fluent state and converted in situ to a non-fluent state.

18. The method of claim 17 wherein the polymer is polymerized in situ by application of a stimulus.

19. The method of claim 18 wherein the stimulus is light, temperature change, exposure to ions, addition of a catalyst or initiator, or radiation.

20. The method of claim 1 further comprising mechanically compressing the voids.

21. The method of claim 20 wherein the voids are compressed by expansion of a balloon catheter in the urethra.

22. The method of claim 21 further comprising mechanically closing the voids.

23. A kit for treating prostate disease comprising making an incision into the prostate, reducing the volume of the prostate by removing endomural tissue to form at least one void in the prostate, and closing the voids in the prostate, wherein an adhesive material is applied within the void prior to closure or a supportive material is applied to the urethra lining to provide structural support, comprising a catheter suitable for insertion into the urethra comprising means for making a transurethral incision, means for cutting and morselating tissue, one or more lumens for administration of an adhesive material or a supportive material to the urethra, means for removal of morselated tissue, and a biocompatible, biodegradable material suitable for administration within the prostate to adhere tissue or within the urethral to provide structural support.

24. The kit of claim 23 wherein the biocompatible, biodegradable material is a solution forming an adhesive polymer in situ following application.

25. The kit of claim 23 wherein the biocompatible, biodegradable material is a solution forming a structurally supportive lining in the urethra following application.

26. The kit of claim 23 wherein the biocompatible, biodegradable material is a conformable solid that can be inserted into the urethra and conformed to the surface to form a barrier or support structure.

27. The kit of claim 23 further comprising bioactive agents for administration to the urethra or voids within the prostate.

28. The kit of claim 27 wherein the bioactive agents are selected from the group consisting of drugs, genes, cells, and molecules altering cellular adhesion.

29. The kit of claim 28 wherein the drugs are selected from the group consisting of antibiotics, antivirals, antiinflammatories, hormones, antineoplastics, antispasmodics, modulators of cell-extracellular matrix interactions, enzymes, enzyme inhibitors, anticoagulants, growth factors, DNA, RNA and protein synthesis inhibitors, anti-cell migratory agents, and vasodilating agents.

30. The kit of claim 29 wherein the drugs are selected from the group consisting of hormones and chemotherapeutic agents.

31. The kit of claim 23 wherein material applied to the voids or urethra lining is a polymer.

32. The kit of claim 31 wherein the polymer is a biodegradable polymer.

33. The kit of claim 32 wherein the polymer is conformable by a change in temperature or mechanical forces in situ.

34. The kit of claim 32 wherein the polymer is in a fluent state which is convertible in situ to a non-fluent state.

35. The kit of claim 34 wherein the polymer is polymerized in situ by application of a stimulus.

36. The kit of claim 35 wherein the stimulus is light, temperature change, exposure to ions, addition of a catalyst or initiator, or radiation.

37. The kit of claim 23 wherein the catheter further comprises expansion means.

38. The kit of claim 37 wherein the catheter further comprises means for suturing or stapling.

39. The kit of claim 23 wherein the catheter further comprises means for generating light, radiation or a temperature change in the voids or urethra.

40. The kit of claim 23 wherein the catheter further comprises means for conforming a lining within the urethra.

41. The kit of claim 23 wherein the catheter further comprises suction or vacuum means.

* * * * *